US009821141B2

(12) United States Patent
Stice et al.

(10) Patent No.: US 9,821,141 B2
(45) Date of Patent: Nov. 21, 2017

(54) MACROPOROUS CATHETER

(71) Applicant: Twin Star Medical, Inc., Minneapolis, MN (US)

(72) Inventors: James D. Stice, North Oaks, MN (US); Scott R. Wilson, Maple Grove, MN (US); Rick Matthew Odland, Roseville, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 0 days.

(21) Appl. No.: 13/789,994

(22) Filed: Mar. 8, 2013

(65) Prior Publication Data

US 2014/0031741 A1 Jan. 30, 2014

Related U.S. Application Data

(60) Provisional application No. 61/676,008, filed on Jul. 26, 2012.

(51) Int. Cl.
*A61M 25/00* (2006.01)
*A61B 10/00* (2006.01)
(Continued)

(52) U.S. Cl.
CPC ..... *A61M 25/0043* (2013.01); *A61B 10/0045* (2013.01); *A61L 29/00* (2013.01);
(Continued)

(58) Field of Classification Search
CPC .......... A61M 25/0009; A61M 25/0043; A61M 2025/0057; A61M 25/0069; A61M 27/00
(Continued)

(56) References Cited

U.S. PATENT DOCUMENTS 5,425,723 A * 6/1995 Wang .................. A61M 25/007
138/114
5,498,251 A * 3/1996 Dalton .......................... 604/523
(Continued)

FOREIGN PATENT DOCUMENTS

EP 0370785 A1 5/1990
FR 2955034 A1 7/2011
(Continued)

OTHER PUBLICATIONS

Helical Hollow Strand™ brochure [online]. Fort Wayne Metals Research Products Corp. [retrieved on Mar. 10, 2015]. Retrieved from the Internet <URL:http://fwmetals.com/products/strands-and-cables/>, two pages: first page No. 6.4 and second page includes a table titled, "Manufacturing Illustration HHS" and graph titled, "HHS Design Parameters".

(Continued)

*Primary Examiner* — Rebecca E Eisenberg

(57) ABSTRACT

The present invention provides a catheter for use in delivering and/or recovering materials to and/or from a tissue site in the body, the catheter comprising one or more macroporous regions adapted to selectively deliver molecules and/or recover cells from the tissue site, based on one or more physical-chemical-biological characteristics. The macroporous region can be provided in the form of a helical hollow wires, and can be adapted to both recover cells from the tissue site (e.g., bacterial or other cells present in interstitial fluid) and optionally to permit the infusion of medicament to the site, under corresponding conditions.

16 Claims, 4 Drawing Sheets

(51) Int. Cl.

| | |
|---|---|
| ***A61L 29/00*** | (2006.01) |
| *A61M 27/00* | (2006.01) |
| *A61B 5/00* | (2006.01) |
| *A61M 1/28* | (2006.01) |
| *A61M 31/00* | (2006.01) |

(52) U.S. Cl.
CPC ........ *A61M 25/00* (2013.01); *A61M 25/0009* (2013.01); *A61M 25/0069* (2013.01); *A61B 5/6846* (2013.01); *A61B 2010/008* (2013.01); *A61M 1/285* (2013.01); *A61M 27/00* (2013.01); *A61M 31/00* (2013.01); *A61M 2025/0057* (2013.01); *Y10T 29/49826* (2015.01)

(58) Field of Classification Search
USPC ............ 604/164.01, 264, 256, 508, 523–526
See application file for complete search history.

(56) References Cited

U.S. PATENT DOCUMENTS

| | | | |
|---|---|---|---|
| 6,030,358 | A | 2/2000 | Odland |
| 6,350,253 | B1 | 2/2002 | Deniega et al. |
| 6,537,241 | B1 | 3/2003 | Odland |
| 6,626,885 | B2 | 9/2003 | Massengale |
| 6,942,633 | B2 | 9/2005 | Odland |
| 6,942,634 | B2 | 9/2005 | Odland |
| 7,004,923 | B2 | 2/2006 | Deniega et al. |
| 7,465,291 | B2 | 12/2008 | Massengale |
| 7,717,871 | B2 | 5/2010 | Odland |
| 7,780,638 | B1 | 8/2010 | Deniega et al. |
| 7,935,092 | B1 | 5/2011 | Odland et al. |
| 7,959,623 | B2 | 6/2011 | Massengale |
| 8,260,411 | B1 | 9/2012 | Odland et al. |
| 8,328,771 | B2 | 12/2012 | Massengale |
| 8,388,584 | B2 | 3/2013 | Odland |
| 2003/0045866 | A1 | 3/2003 | Petersen |
| 2004/0236309 | A1 | 11/2004 | Yang |
| 2005/0165342 | A1 | 7/2005 | Odland |
| 2007/0060834 | A1 | 3/2007 | Odland et al. |
| 2009/0270841 | A1 | 10/2009 | Lentz |
| 2009/0287178 | A1 | 11/2009 | Herbert |
| 2010/0100061 | A1 | 4/2010 | Odland |
| 2010/0106140 | A1 | 4/2010 | Odland et al. |
| 2010/0286586 | A1 | 11/2010 | Odland |
| 2011/0178505 | A1 | 7/2011 | Odland et al. |
| 2012/0172791 | A1 | 7/2012 | Odland |
| 2012/0238872 | A1* | 9/2012 | Schwager ..................... 600/434 |

FOREIGN PATENT DOCUMENTS

| | | | |
|---|---|---|---|
| WO | 9200113 | A1 | 1/1992 |
| WO | 9426341 | A1 | 11/1994 |
| WO | 9907276 | A2 | 2/1999 |
| WO | 0105210 | A2 | 1/2001 |
| WO | 0230488 | A2 | 4/2002 |
| WO | 03082074 | A3 | 10/2003 |
| WO | 2007003431 | A1 | 1/2007 |
| WO | 2008092090 | A2 | 10/2008 |
| WO | 2008098207 | A3 | 10/2008 |
| WO | 2009061927 | A1 | 5/2009 |
| WO | 2010005714 | A1 | 1/2010 |
| WO | 2010031515 | A1 | 3/2010 |
| WO | 2011150359 | A1 | 12/2011 |
| WO | 2012177765 | A2 | 12/2012 |
| WO | 2014018595 | A1 | 1/2014 |

OTHER PUBLICATIONS

Notification of Transmittal of the International Search Report and the Written Opinion of the International Searching Authority, or the Declaration of PCT/US2013/051776 dated Oct. 24, 2013, 16 pages, European Patent Office, Rijswijk, The Netherlands.

Tahlil, Ouafae et al., "The Dispatch™ Catheter as a Delivery Tool for Arterial Gene Transfer," Cardiovascular Research (1997) pp. 181-187, vol. 33, Oxford University Press.

* cited by examiner

Effective Length

Effective Length

Section B-B

MACROPOROUS CATHETER

TECHNICAL FIELD

The present invention relates to catheters adapted to be positioned in tissue sites within the body, including those used for delivering and/or withdrawing materials such as fluids, molecules, particles, and cells to and from the body.

BACKGROUND OF THE INVENTION

Various sites within the body are difficult to access by minimally invasive means, e.g., in order to take biopsy or other samples, or for delivering materials to the site locally. Tissue sites that include infections of the skin and soft tissue, such as cellulitis, typically cannot be cultured, although tissue biopsy, fine needle aspiration, and blood cultures have been attempted. It is occasionally possible to recover bacteria from such sites by means of fine needle aspiration, with the best recovery in conditions of excess tissue fluid, such as congestive heart failure and kidney disease. When used to aspirate tissue or fluids, by the use of negative pressure, needles tend to entrap tissue, thereby preventing ingress of interstitial fluid. Without the ability to quickly access and sample such sites, however, the corresponding identification of the pathogen, and in turn treatment, are often delayed, or not possible at all. There exists a need for the recovery of samples in such circumstances, including the recovery of bacteria from sites in which no ulceration, abscess pocket, or other drainage site might exist.

On another subject, a wide array of devices have been described for use in delivering fluids and compounds (e.g., molecules) to the body, e.g., by means that include anything from direct inoculation or injection to prolonged infusion. Relatively few of these devices are particularly well suited for the prolonged infusion of large molecules (e.g., macromolecules), particularly to regions of the body that are relatively less accessible to needles and the like.

For instance, Tahlila et al. describe the manner in which arterial gene therapy requires efficient local gene delivery to the cells of the arterial wall ("The Dispatch™ catheter as a delivery tool for arterial gene transfer", Cardiovascular Research, 33(1):181-187). Various vectors can be used, and can be delivered percutaneously using a host of delivery devices, such as double balloon catheters, hydrogel-coated balloon catheters, porous balloon catheters, and 'channeled' balloon catheters.

On yet another subject, catheters have long existed for various applications within the body. Applicant has itself become a world leader in the field of catheters having microporous portions (e.g., in the form of "hollow fibers"), for use in various embodiments. See, for instance, U.S. Pat. Nos. 6,030,358; 6,537,241; 6,942,633; 6,942,634; 7,717,871; and 7,935,092; and U.S. Publication Nos. US-2005-0165342-A1; US-2007-0060834-A1; US-2010-0100061-A1; US-2010-0106140-A1; and US-2010-0286586-A1; the disclosures of each of which are incorporated herein by reference.

SUMMARY OF THE INVENTION

The present invention provides a catheter that comprises one or more macroporous regions suitable for insertion in a body tissue site in order to deliver and/or recover materials (e.g., fluid, molecules, particles, and/or cells) to and/or from the tissue, and which is then subsequently suitable for safe removal from the tissue site.

In a preferred embodiment, the invention provides a catheter for use in delivering and/or recovering materials to and/or from a tissue site in the body, the catheter comprising one or more macroporous regions adapted to selectively deliver and/or recover materials such as molecules and cells to and from the tissue site, based on one or more physical-chemical-biological characteristics. The catheter can include one or more macroporous regions selected from the group consisting of inorganic (e.g., metallic) and/or polymeric structures, such as helical hollow wires, that can be adapted to both recover bacterial cells from the tissue site and permit the infusion of therapeutic fluids (e.g., containing medicament) to the site, under corresponding conditions (e.g., the application of positive or negative pressure).

The invention further provides a corresponding method of preparing and using a catheter as described herein, including for the sampling and/or identification of bacterial infection within an otherwise inaccessible tissue site, and in turn, optionally for the treatment of such infection by the delivery of medicament through the same catheter, preferably while in position within the tissue site.

In a preferred embodiment, the catheter comprises a combination of a catheter body and one or more macroporous regions, preferably hollow macroporous regions, which can be provided in any suitable combination and arrangement, to provide a catheter having sufficient structural integrity for the macroporous region(s) to be positioned within a tissue site, optionally without the need for ancillary devices such as introducers or protective sheaths, and to there be used for the purpose of delivering and/or recovering materials to and/or from the surrounding tissue, with the catheter itself thereafter being capable of removal from the tissue site.

In one such embodiment, the catheter body will include a substantially solid body portion that is coupled with and extends proximally from a generally hollow macroporous region(s). The catheter will have sufficient properties (e.g., strength, flexibility and patency) to permit the hollow macroporous region(s) to be placed, to remain in place, and to be used for their intended purpose. In a particularly preferred embodiment, the macroporous region is itself non-inflatable, as compared for instance to an inflatable balloon that might provide the desired porosity once positioned and inflated within the body. Optionally, however, the macroporous region is sufficiently (and ideally reversibly) expandable or flexible, e.g., to permit its porosity to be altered, for instance, in order to dislodge clogged pores while positioned within the tissue site. In one preferred embodiment, the catheter can be used, for instance, to remove bacteria from infected tissue in a minimally invasive manner, thereby allowing for fast and accurate diagnosis and proper treatment of skin and soft tissue infections. In an alternative preferred embodiment, the catheter can be used, for instance, for the delivery (e.g., by infusion) of medicaments that are themselves not amenable to either direct delivery (as by syringe) or prolonged delivery (as by infusion).

In one preferred embodiment, the catheter can comprise a removable rigid stylet, for instance, to reinforce the catheter for insertion into tissue, e.g., by positioning the stylet within the catheter. It is generally desirable to remove the rigid stylet after positioning the catheter in the targeted tissue, so as to minimize tissue trauma from inadvertent movement of the catheter with a rigid stylet. In this manner, the catheter, including the macroporous region(s), can be retained in position after positioning of the catheter into body tissue using the rigid stylet, and prior to treatment (e.g., delivery and/or removal of fluid, fluid components, and cells).

The macroporous region(s), in turn, will be of sufficient type, size, dimensions, configuration and porosity to permit them to be positioned, and to remain positioned, within a body tissue, including in the course of stylet removal, and there used to deliver or recover materials (e.g., fluid, molecules, and/or cells). The hollow macroporous region(s) can in the form of a microtube, that can be coupled to one or more positioning and/or reinforcing component(s) and/or to the catheter body at or near its proximal end, and extend distally therefrom.

Similarly, a catheter of the present invention is, or can be adapted to be sufficiently steerable to permit the user to direct the distal end in vivo. Various approaches for imparting directional control to the distal tip (macroporous regions(s)) will become apparent to those skilled in the art, given the present description, and are incorporated herein by reference.

In a particularly preferred embodiment, the invention provides a catheter comprising one or more macroporous regions, preferably in the form of a contiguous hollow region, such as a stranded wire. The word "macroporous" as used herein, will refer generally to a surface having sufficient porosity to permit desired fluid, fluid components, molecules (e.g., medicaments), and/or cells, to be delivered and/or recovered through the portion and in fluid contact with the lumen of the catheter. Such porosity can be based upon any principle, including size exclusion, and/or based upon other physical, chemical, or biological characteristics (e.g., by the use of binding agents, lubricious, or other coatings).

In a particularly preferred embodiment, the proposed catheter comprises a macroporous portion having pores that are large enough to recover bacteria, which can then be quickly analyzed via molecular and/or other mechanisms to determine the species, strain, drug resistance, and virulence. Once identified, the proper medicament (e.g., antibiotic) can be identified and delivered directly to the body, either by conventional means (e.g., systemically), or optionally and preferably, directly to the same tissue site by means of the still positioned catheter of this invention. Direct tissue infusion of antibiotic can significantly increase local tissue concentration and reduce systemic complications.

Suitable materials for use in providing the macroporous region of a catheter of this invention can be provided in any suitable form. Commercially available materials include those identified as helical hollow strands, and are available, for instance, from Fort Wayne Metals. Such materials are provided in the form of stranded wire having an open center working channel, and can be constructed from various material types (e.g., having desired properties, such as modulus). Suitable material types for use in preparing a macroporous catheter region include, for instance, nitinol, platinum, titanium, and are available commercially (e.g., as style nos. 302, 304V and 316L, as shown on www.fwmetals.com.

In turn, those skilled in the art, given the present description, will appreciate the manner in which a macroporous region of this invention can be designed to any desired specifications, e.g., in terms of dimensions, tension, compression, torque, and pitch strength. So too can single, dual and triple layer tubes can be prepared as well, having desired flexibility and control, and providing suitable inner diameter, outer diameter, wire size, and filar diameter, filar number. For instance, a hollow helical strand can be provided with an inner diameter between about 0.02 mm to about 3.5 mm, an outer diameter between about 0.06 mm to about 5 mm, about 6 to about 18 filars, and a pitch selected from left, right, unidirectional, and reverse pitch. These and other characteristics, in turn, can be used to provide one or more macroporous regions having desired properties, particularly including size characteristics, porosity, and compatibility with the body.

A catheter, including macroporous region, of this invention can be modified, e.g., coated, in order to provided desired properties, such as lubricity, hydrophobicity or hydrophilicity, and hemocompatability.

A macroporous region is preferably tubular, and can be used to controllably permit the recovery and/or delivery of any desired materials through the tubular walls, including for instance, materials selected from the group consisting of fluid (including relatively small solutes with or without encapsulates), macromolecules (e.g., proteins and nucleic acids with or without encapsulates), viruses, and cells, including sub-cellular components, cell particulate, whole cells (e.g., bacterial cells, blood cells) and combinations of cells (e.g., agglomerated cells). Given the present description, those skilled in the art will understand the manner in which the selection and use of a macroporous region can depend on various factors, including for instance, the molecular weight, configuration, and physical-chemical characteristics of the macromolecules to be recovered or delivered, as well as on the various dimensions and properties of cells and corresponding subparts and combinations thereof.

By contrast, the use of "microporous" hollow fiber (tubular) membranes can, of the type described in the Background section above, can at times be constrained by various factors, including by the lack of available fibers with various (and particularly large) porosities, as well as by the structural integrity of the fibers themselves, which tend to have very small diameters. The use of such fibers for in vivo applications can in turn be limited, under certain conditions, e.g., by the tendency of both the walls and lumen of such fibers to themselves become occluded or fouled, particularly under conditions of high concentrations of large molecules (e.g., albumin) and/or large volume infusions or aspirations. For these and other reasons, the use of conventional microporous hollow fiber members is typically limited to those having an effective upper most porosity of between 0.45 to 0.5 microns. This corresponds well with conventional 'microfiltration', as by the use of conventional (and generally non-tubular) membranes, for instance, having standard pore sizes that typically include 0.1, 0.2, 0.45 microns, though which can also include those having pore sizes of 0.65, 1 and 5 microns, depending on a wide array of factors (including the application for which they are used). See, for instance, "Ultrafiltration—Application and Product Guide", Millipore.

By contrast, a macroporous region of the present invention can provide effective porosity of 0.5 microns and greater, as by the use of helical hollow strands that can be constructed in order to provide an average porosity of about 0.5 microns, about 5 microns, about 10 microns, about 20 microns, about 30 microns, about 40 microns, about 50 microns, about 60 microns, about 70 microns, about 80 microns, about 90 microns, or about 100 microns. Given its preferred tubular structure, and the optional ability to limit or address fouling as described herein, the macroporous region of this invention can be used for applications that conventional hollow fibers are not generally suitable, such as for sampling interstitial fluid for the presence of bacteria or viruses.

The "pore size" as used to describe a macroporous region of the present catheter will typically be provided in functional terms, as the porosity required to effectively permit the recovery and/or delivery of desired materials under the conditions of use. In turn, pore size can be provided as a micron value, indicating that particles larger than the rating will be precluded from passing into or through the region wall. The porosity can be rated as well in terms of the nominal molecular weight limit (NMWL), also sometimes referred to as the molecular weight cut-off. The NMWL indicates that most dissolved macromolecules with molecular weights higher than the NMWL will not be able to pass through the wall of the region. Those skilled in the art will appreciate the manner in which the selected porosity cut off will typically be well below the molecule weight of the solute(s) to be excluded. The ability of a desired material to be precluded by or delivered through the region wall will be a function of a variety of factors, including the molecular shape and size of the material (e.g., molecule, particle or cell), electrical characteristics, fluid or tissue concentration and composition, operating conditions, and device or system configuration. So too will performance be affected by parameters such as pressure, concentration, temperature, pH, and potential fouling.

DETAILED DESCRIPTION

Figures 1, 2, 3:
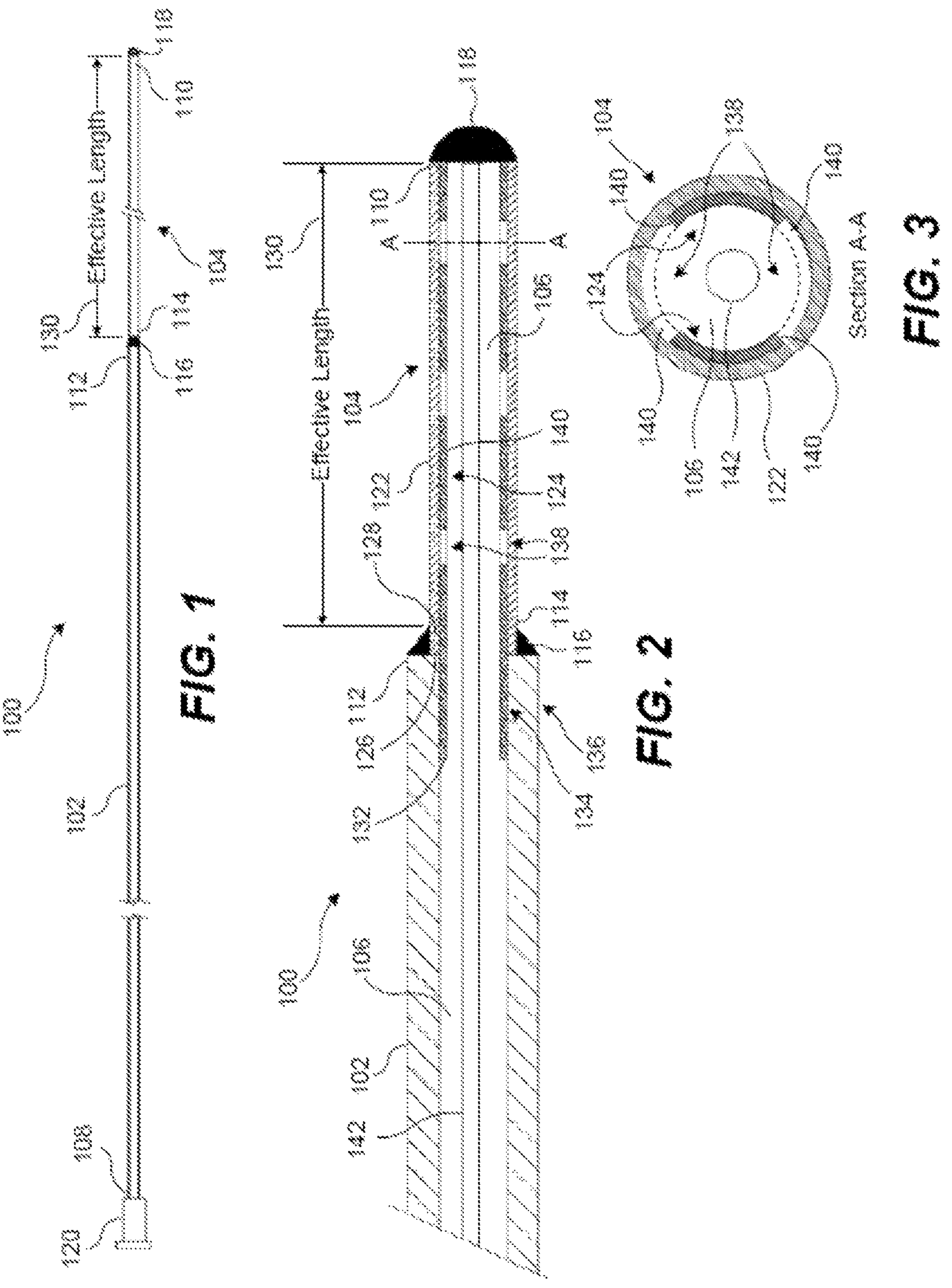
FIG. 1 illustrates a catheter in accordance with an embodiment of the invention.
FIG. 2 is a longitudinal cross-sectional view of a distal region of the catheter of FIG. 1.
FIG. 3 is a transverse cross-sectional view along section A-A in the distal region shown in FIG. 2.

While multiple embodiments of the invention are disclosed herein, still others may become apparent to those skilled in the art. In the following, certain illustrative and non-limiting embodiments are described in detail with reference to the accompanying drawings wherein like elements are designated by like numerals. It should be clearly understood that there is no intent, implied or otherwise, to limit the invention in any form or manner to that described herein. As such, all alternative embodiments are considered as falling within the spirit, scope and intent of the disclosure. The metes and bounds of the invention is defined by the appended claims and any and all equivalents thereof.

SELECTED NOMENCLATURE

100 catheter
102 catheter body
104 macroporous section
106 lumen within catheter 100
108 proximal end of catheter 100 (catheter body 102)
110 distal end of catheter 100 (macroporous section 104; macroporous coil 122; internal support tube 124)
112 distal end of catheter body 102
114 proximal end of macroporous section 104
116 seal between catheter body 102 and macroporous section 104 (macroporous coil 122)
118 end piece
120 connector at proximal end of catheter 100 (catheter body 102)
122 macroporous coil
124 internal support tube
126 proximal end of macroporous coil 122
128 proximal region of macroporous coil 122
130 effective or exposed length of macroporous coil 122
132 proximal end of internal support tube 124
134 proximal region of internal support tube 124
136 distal region of catheter body 102
138 openings such as slots or perforations in internal support tube 124
140 wall of internal support tube 124
142 core wire
200 catheter (alternate embodiment)
204 macroporous section
300 catheter (alternate embodiment)
344 tube within lumen 206 of catheter 300
346 openings such as slots or perforations through wall 348 in distal region 350 of tube 344
348 wall of tube 344
350 distal region of tube 344
352 lumen within tube 344
354 infusion flow paths
356 aspiration flow paths
400 self-introducing catheter
402 catheter body
404 macroporous section of catheter 400
406 longitudinally extending lumen within catheter 400
408 distal region of catheter 400
410 distal end of catheter 400
414 proximal end of macroporous section 404
416 medical grade adhesive, weld, braze, solder joint
418 end piece of catheter 400
430 effective length of macroporous section 404
442 stylet within catheter 400
446 openings such as slots or perforations in distal region 450 of catheter body 402
448 wall of distal region 450 of catheter body 402
450 distal region of catheter body 402

FIG. 1 illustrates an embodiment of elongate catheter 100 configured for delivering or recovering fluid and/or material, including medicament, to or from a tissue site in a body. FIG. 2 is a longitudinal cross-sectional view of a distal region of catheter 100; and FIG. 3 is a transverse cross-sectional view along section A-A in the distal region shown in FIG. 2. Catheter 100 is defined, at least in part, by interconnected catheter body 102 and macroporous section 104 having lumen 106 extending longitudinally there through between proximal and distal ends 108 and 110. Proximal and distal ends 108 and 110, respectively, further define a proximal end of catheter body 102 and a distal end of macroporous section 104. Catheter body 102 extends longitudinally between proximal and distal ends 108 and 112, and macroporous section 104 extends longitudinally between proximal and distal ends 114 and 110. In general, catheter body 102 is made of any suitable flexible medical grade tubing material such as stainless steel or other metals, urethane, polymers, or fiber reinforced composites as will become apparent to those skilled in the art. While catheter 100 in general, and both catheter body 102 and macroporous section 104 in particular, are illustrated as having circular cross-sections, this does not always have to be the case. For instance, in some non-limiting exemplary embodiments, the one or more cross-sections are elliptical, triangular, square, rectangle, or any other geometrical shape. Also, catheter body 102 and macroporous section 104 can have the same or distinctly different cross-sections.

As shown, catheter body 102 and macroporous section 104 are interconnected by securely attaching respective distal and proximal ends 112 and 114 to one another and forming seal 116 using a suitable medical grade adhesive as will become apparent to those skilled in the art, including an epoxy or urethane, or using a weld, braze or solder joint when metallic material are used. Catheter 100 includes end piece 118 such as a plug having a blunt or a sharp tip or a trocar or a stylet securely attached thereto for inhibiting the flow of any fluid and/or material into or out of lumen 106 across distal end 110. Proximal end 108 includes connector 120 configured for removably attaching (or connecting) catheter 100 to a medical device (not shown) and providing fluid connectivity with lumen 106. Accordingly, in some embodiments of catheter 100, connector 120 is a leur connector or a leur lock fitting as will become apparent to those skilled in the art.

In some embodiments of catheter 100, macroporous section 104 is defined, at least in part, by macroporous coil 122 longitudinally circumscribing at least a portion of an outer surface of internal support tube 124. As illustrated, distal end 110 of catheter 100 (and of macroporous section 104) further defines a distal end of both macroporous coil 122 and internal support tube 124. Macroporous coil 122 extends longitudinally between proximal and distal ends 126 and 110 with at least a portion of proximal region 128 covered by seal 116 whereat catheter body 102 connects with (or attaches to) macroporous section 104. As such, effective (or exposed) length 130 defines, at least in part, a longitudinal extent of macroporous coil 122 (or macroporous section 104) through which fluid and/or material can be delivered or recovered to or from a tissue site.

In accordance with an embodiment of the invention, macroporous coil 122 is a tube having a porous wall made from filars, defining, at least in part, an open center working channel. As such, the porosity of macroporous coil 122, or the ease with which, a fluid and/or material travels across the porous wall between an inner and an outer surface of macroporous coil 122 can be affected by, for example, one or more of the number of filars, a diameter of each one of the one or more filars, the distance (or spacing) between a surface of each one of the one or more filars, or any combination thereof. For instance, the porosity of macroporous coil 122 can be increased or decreased, respectively, by increasing or decreasing the distance between the surfaces of adjacent filars. Similarly, increasing or decreasing the diameter of the one or more filars can affect the porosity of macroporous coil 122. One such device useable as macroporous coil 122 is sold under the trade name Helical Hollow Strand Tube (HHS® Tube) by Fort Wayne Metals; Fort Wayne, Indiana; USA (http://www.fwmetals.com/hhs-wire.php).

In some embodiments of macroporous section 104, lumen 106 is defined, at least in part, by internal support tube 124 positioned within the open center working channel of macroporous coil 122. As shown, internal support tube 124 extends longitudinally between proximal and distal ends 132 and 110, with proximal region 134 extending into at least a portion of lumen 106 extending through distal region 136 of catheter body 102. In a non-limiting exemplary embodiment of catheter 100, internal support tube 124 is a tube having one or more openings such as slots or perforations 138 through wall 140 thereof, with the outer surface of internal support tube 124 in contact with an inner surface of both macroporous coil 122 and distal region 136 of catheter body 102. Accordingly, any fluid and/or material introduced under pressure into lumen 106 will flow distally through lumen 106, through openings 138, through the porous wall of macroporous coil 122, and into the area (not shown) surrounding macroporous section 104. And, fluid and/or material in the area surrounding macroporous section 104 can be extracted by applying a vacuum in lumen 106 causing the fluid and/or material to flow from the surrounding area, through the porous wall of macroporous coil 122, through openings 138, into lumen 106, and out proximal end 108 (or connector 120) of catheter 100. As such, openings 138 are configured and positioned (or distributed) along the longitudinal extent of macroporous section 104 in a manner conducive for enabling even (or equal) flow of fluid and/or material through the porous wall of macroporous coil 122.

Internal support tube 124 serves to protect or reinforce at least a distal region of catheter 100 defined, at least in part, by macroporous coil 122 and distal region 136 of catheter body 102 into which it extends. In some embodiments, internal support tube 124 is made of or fabricated from polymer or metal or metallic wire having sufficient strength and flexibility for maneuvering the distal region of catheter 100. In a non-limiting exemplary embodiment, internal support tube 124 is rigid and, as such, is configured for providing rigidity and support for the distal region of catheter 100. In other embodiments, internal support tube 124 is flexible and, as such, is configured for providing reinforcement and support for macroporous coil 122 and distal region 136 of catheter body 102 into which it extends. In some embodiments of internal support tube 124, openings 138 are one or more of circles, ellipses, triangles, squares, rectangles, or any other geometrical shape as may be need to provide the necessary porosity, strength and flexibility.

While the rigidity and support provided by macroporous coil 122 and/or internal support tube 124 may be sufficient for the introduction into or penetration of relatively soft tissues, a more stiffened distal region of catheter 100 may be desirable or necessary for other applications such as for the introduction into or penetration of relatively hard tissues. Accordingly, some embodiments of catheter 100 include elongate core wire 142 extending longitudinally within lumen 106 between proximal and distal ends 108 and 110. As such, core wire 142 is of sufficient rigidity to facilitate the introduction or penetration of catheter 100 into the tissue. In some embodiments, core wire 142 is a stylet configured for imparting rigidity to catheter 100. In other embodiments, a distal end of core wire 142 is attached or secured to end piece 118 and, as such, facilitates both the insertion and removal of catheter 100. In yet other embodiments, the distal end of core wire 142 is not secured or attached to end piece 118 and is therefore extractable or removable from catheter 100 after macroporous section 104 has been positioned at the target tissue as desired. In certain embodiments of the invention, core wire 142 is a hollow tube defining a lumen therewithin.

While FIGS. 1-3 illustrate an embodiment of catheter 100 wherein macroporous coil 122 longitudinally circumscribes at least a portion of the outer surface of internal support tube 124, this does not always have to be the case. For instance, in some embodiments of the invention (not shown), macroporous coil 122 and internal support tube 124 are radially spaced apart along at least a portion of their respective longitudinal extent within macroporous section 104. In other embodiments of the invention (also not shown), the distal end of internal support tube 124 does not extend to (or coincide with) distal end 110 of catheter 100. In one such embodiment, the distal end of internal support tube 124 terminates proximally of distal end 110 of catheter 100; whereas in other such embodiments, an additional elongated member bridges a gap between the distal end of internal support tube 124 and distal end 110 of catheter 100. In yet other embodiments of the invention (also not shown), the distal ends of both macroporous coil 122 and internal support tube 124 do not extend to (or coincide with) distal end 110 of catheter 100, and an additional elongated member bridges a gap between the distal ends of both macroporous coil 122 and internal support tube 124 and distal end 110 of catheter 100. In another embodiment of the invention (not shown), an external support structure such as a tube or another macroporous coil longitudinally circumscribes an external surface of macroporous coil 122. Generally, the wall of the external support structure will be configured for facilitating the flow of fluids and/or materials thereacross and, as such, will include one or more of a porous structure or one or more openings. In one such embodiment, an internal surface of the external support structure and the external surface of macroporous coil 122 are not radially spaced apart; whereas in other such embodiments, the internal surface of the external support structure and the external surface of macroporous coil 122 are radially spaced apart. In yet another embodiment of the invention, either one or both of internal support tube 124 and the external support structure are either radially spaced apart or are not radially spaced apart from macroporous coil 122.

As can be seen, several alternative configurations are contemplated as being within the spirit, scope and intent of the disclosed invention. Furthermore, additional configurations may become apparent to those skilled in the art. Accordingly, all variations or additional configurations are considered as falling within the metes and bounds of the instant invention.

Figure 4:
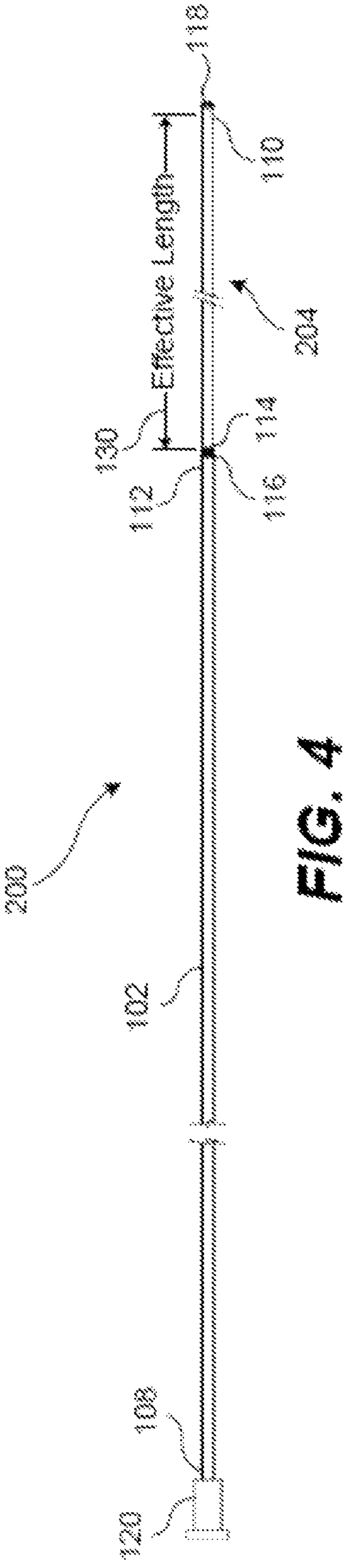
FIG. 4 illustrates a catheter in accordance with an alternate embodiment of the invention.
Figure 5:
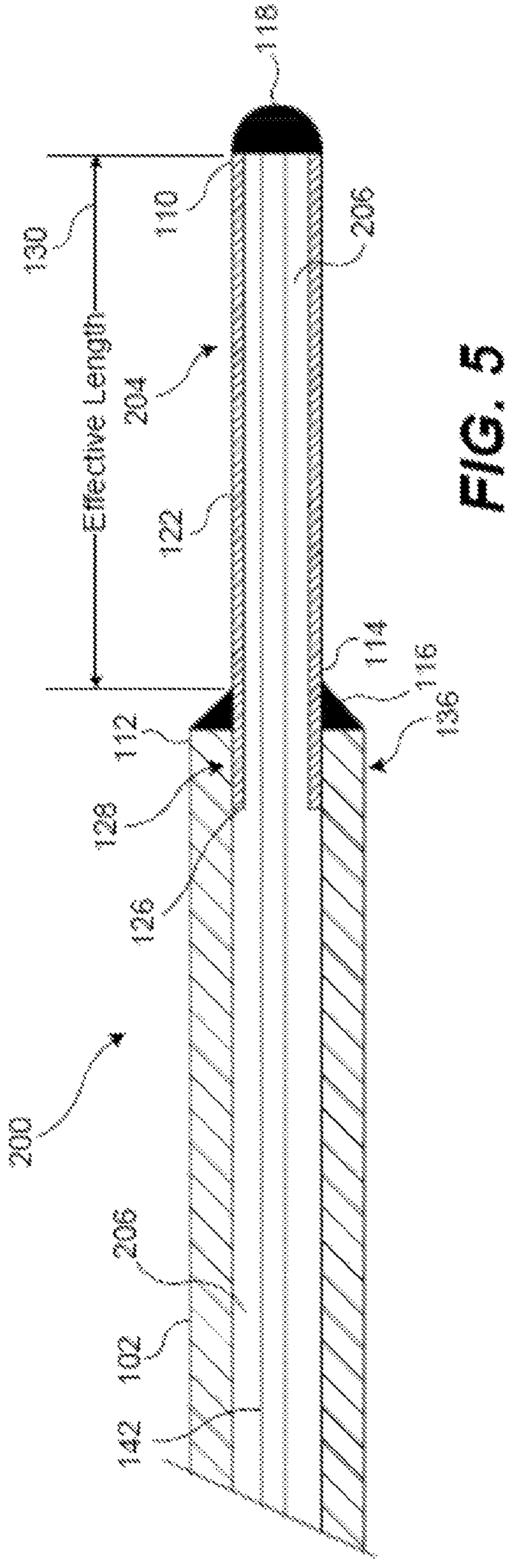
FIG. 5 is a longitudinal cross-sectional view of a distal region of the catheter of FIG. 4.

FIG. 4 illustrates an alternate embodiment of elongate catheter 200 configured for delivering or recovering fluid and/or material to or from a tissue site in a body; and FIG. 5 is a longitudinal cross-sectional view of a distal region of catheter 200. Elements of catheter 200 that are identical to or substantially similar to those of previously described catheter 100 are illustrated with like numerals. Therefore, in the interest of brevity, only those elements of catheter 200 that are substantially different from those of catheter 100 are described in the following.

As shown, catheter 200 is defined, at least in part, by interconnected catheter body 102 and macroporous section 204 having lumen 206 extending longitudinally therethrough between proximal and distal ends 108 and 110. Macroporous section 204 is defined, at least in part, by macroporous coil 122 extending longitudinally between proximal and distal ends 126 and 110. Catheter body 102 and macroporous section 204 are interconnected by inserting at least a portion of proximal region 128 of macroporous coil 122 into lumen 206 extending through distal region 136 of catheter body 102. In some embodiments of the invention, such an insertion forms a snug fit or a reinforced support between macroporous coil 122 and catheter body 102. Macroporous coil 122 and catheter body 102 are securely attached to one another by forming seal 116 using a suitable medical grade adhesive as will become apparent to those skilled in the art, including an epoxy or urethane, or using a weld, braze or solder joint when metallic material are used.

Fluid and/or material introduced into lumen 206 under pressure will flow outwardly from lumen 206, through the porous wall of macroporous coil 122, and into the surrounding tissue. And, fluid and/or material in the surrounding tissue can be extracted by applying a vacuum in lumen 206 causing the fluid and/or material to flow from the tissue, through the porous wall of macroporous coil 122, into lumen 206, and out proximal end 108 (or connector 120) of catheter 200.

While FIGS. 4 and 5 illustrate an embodiment of catheter 200 wherein macroporous section 204 includes only macroporous coil 122 and does not include any additional external or internal support structure or tube such as internal support tube 124 described in the foregoing non-limiting exemplary embodiment with reference to FIGS. 1-3, this does not always have to be the case. As such, alternate embodiments of the invention include catheter 200 wherein an internal support tube is longitudinally circumscribed by macroporous coil 122, or an external support structure longitudinally circumscribes macroporous coil 122, or any combination thereof. Further embodiments of the invention include catheter 200 wherein, either one or both internal and external support structures are either radially spaced apart or are not radially spaced apart from macroporous coil 122. Of course, the walls of all such internal or external support structures are configured for facilitating the flow of fluids and/or materials thereacross and, as such, will include one or more of a porous structure or one or more openings. All alternative and/or additional configurations that may become apparent to those skilled in the art are considered as falling within the metes and bounds of the instant invention.

Figures 6, 7, 8, 9:
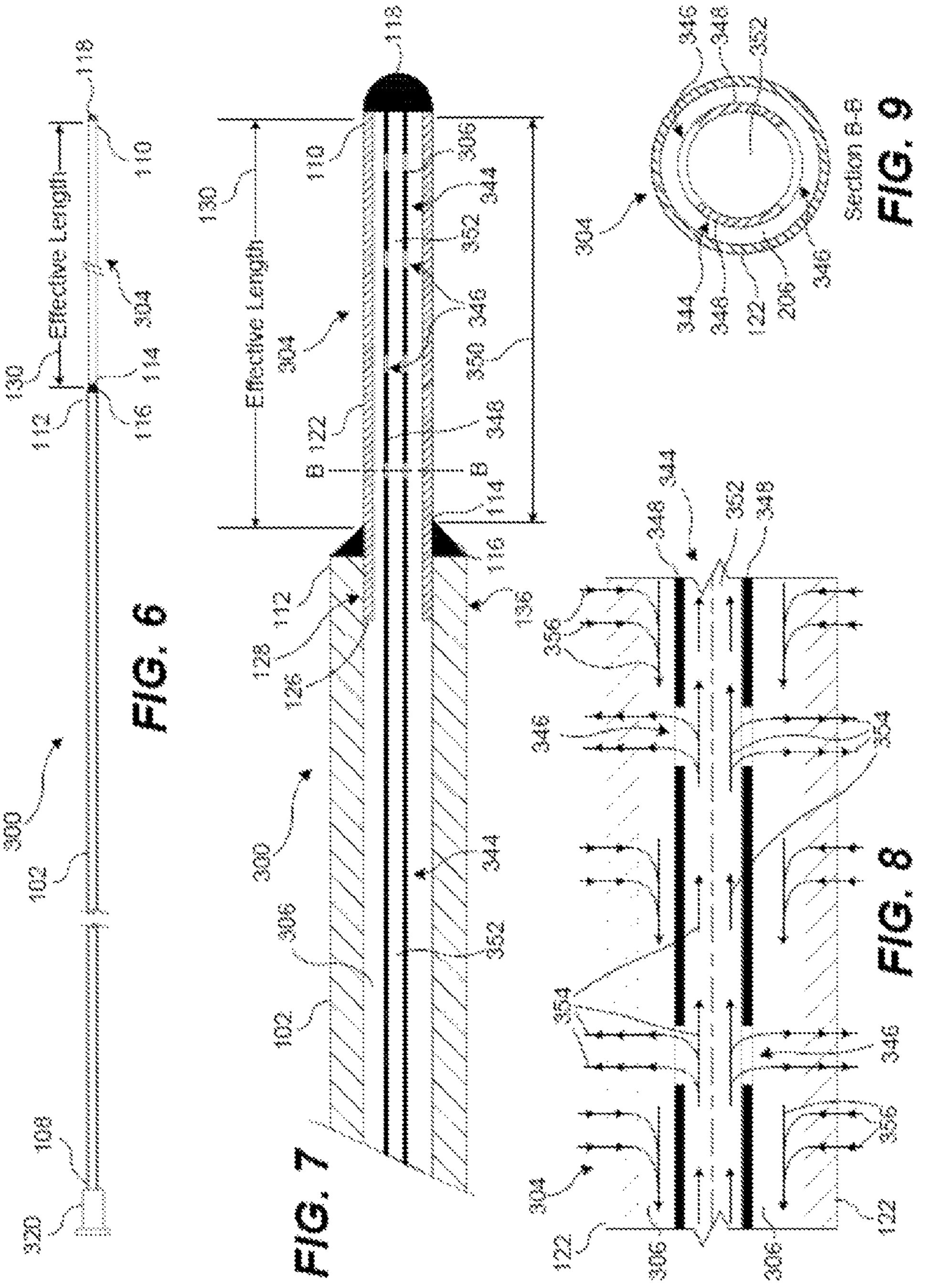
FIG. 6 illustrates a catheter in accordance with another embodiment of the invention.
FIG. 7 is a longitudinal cross-sectional view of a distal region of the catheter of FIG. 6.
FIG. 8 shows exemplary flow paths in a section of the macroporous section of the distal region shown in FIG. 7.
FIG. 9 is a transverse cross-sectional view along section B-B in the distal region shown in FIG. 7.

FIG. 6 illustrates another embodiment of elongate catheter 300 configured for delivering or recovering fluid and/or material to or from a tissue site in a body. FIG. 7 is a longitudinal cross-sectional view of a distal region of catheter 300; FIG. 8 illustrates the flow paths of the fluids and/or material in the macroporous section of catheter 300; and FIG. 9 is a transverse cross-sectional view along section B-B in the distal region shown in FIG. 7. Elements of catheter 300 that are identical to or substantially similar to those of previously described embodiments are illustrated with like numerals. Therefore, in the interest of brevity, only those elements of catheter 300 that are substantially different from those of other embodiments are described in the following.

Catheter 300 is defined, at least in part, by interconnected catheter body 102 and macroporous section 304 having lumen 306 extending longitudinally therethrough between proximal and distal ends 108 and 110. Catheter 300 further includes tube 344 extending longitudinally within lumen 306 between proximal and distal ends 108 and 110. In the illustrated embodiment, tube 344 includes one or more openings such as slots or perforations 346 extending through wall 348 in at least distal region 350 thereof. Lumen 352, extending longitudinally within tube 344 between proximal and distal ends 108 and 110, is configured for fluid communication between openings 346 and connector 320 at proximal end 108 of catheter 300. As shown, macroporous section 304 is defined, at least in part, by distal region 350 of tube 344 in combination with macroporous coil 122. Accordingly, openings 346 in distal region 350 are configured and positioned (or distributed) along a longitudinal extent of tube 344 (and of macroporous section 304) in a manner conducive for even (or equal) flow or distribution of fluid and/or material through the porous wall of macroporous coil 122.

Generally, tube 344 is of sufficient rigidity to facilitate the introduction or penetration of catheter 300 into the tissue. In some embodiments of catheter 300, a distal end of tube 344 is attached or secured to end piece 118 and, as such, facilitates both the insertion and removal of catheter 300. In other embodiments, the distal end of tube 344 is not secured or attached to end piece 118 and is either fully or partially retractable or removable from catheter 300. The terms retractable and removable, as used herein, indicate a movement of the distal end of tube 344 in a proximal direction. In some embodiments of catheter 300 wherein tube 344 is at least partially retractable or removable, the distal end of tube 344 (and of lumen 352 defined thereby) is closed or plugged for inhibiting the flow of fluids and/or materials into or out of lumen 352 through the distal end of tube 344. In other embodiments of catheter 300 wherein tube 344 is at least partially retractable or removable, it may be advantageous or desirable to not close or plug the distal end of tube 344 and therefore permit the flow of fluid and/or material into or out of lumen 352 through the distal end of tube 344. For instance, if or when one or more of openings 346 gets clogged or obstructed, tube 344 can be retracted such that fluid and/or material can continue flowing through its distal end for aspiration or infusion across or through macroporous coil 122. Alternatively, even if or when openings 346 are not clogged or obstructed, it may be desirable or advantageous to increase or decrease the flow of fluid and/or material across or through macroporous coil 122 by at least partially retracting or advancing the distal end of tube 344 away from or towards end piece 118. In certain embodiments of the invention, an increase in the flow of fluids and/or material through lumen 352 of tube 344 may be desirable or advantageous for unclogging macroporous coil 122. In alternate embodiments of the invention, it may be desirable or advantageous to induce clogging or obstruction of openings 346 and/or of macroporous coil 122.

In some embodiments of the invention, catheter 300 includes core wire 142 as described in the foregoing non-limiting exemplary embodiments with reference to FIGS. 1-3. In one such embodiment, the core wire extends longitudinally within lumen 352 of tube 344; whereas in another such embodiment, the core wire extends longitudinally within lumen 306 of catheter 300. As previously described, core wire 142 is a stylet configured for imparting at some level of stiffness and rigidity in some embodiments of catheter 300. In alternate embodiments of catheter 300, core wire 142 is a hollow tube defining a longitudinally extending lumen therewithin, wherein a distal region of core wire 142 may or may not include openings such as openings 346 through a wall of the tube.

In accordance with an embodiment of the invention, catheter 300 is configured for facilitating both aspiration and infusion of fluid and/or material from or to the tissue site whereat macroporous section 304 is positioned. Infusion generally includes the delivery of medicament or flushing with a saline solution; and aspiration generally includes the extraction of fluids and/or material from the surrounding tissue or a diseased site and from within the catheter or the lumen therein. Accordingly, connector 320 is a luer connector or a connector having two separate fittings, wherein one fitting is in fluid communication with lumen 306 of catheter 300 and the other fitting is in fluid communication with lumen 352 of tube 344 within catheter 300. As such, the connector with two separate fittings can be a Y-connector. In some embodiments of catheter 300, lumen 306 is used for aspiration by applying a vacuum at the corresponding fitting in connector 320, and lumen 352 is used for infusion by injecting a fluid and/or material under pressure at the corresponding fitting in connector 320. In other embodiments of catheter 300, the functionalities of lumens 306 and 352 are reversed in that lumen 306 is used for infusion by injecting a fluid and/or material under pressure at the corresponding fitting in connector 320, and lumen 352 is used for aspiration by applying a vacuum at the corresponding fitting in connector 320. In some embodiments of the invention, when one of lumen 306 or 352 is used for aspiration, the other lumen not being used for aspiration is closed off in order to inhibit any "short circuiting" between the lumens. Similarly, when one of lumen 306 or 352 is used for infusion, the other lumen not being used for infusion is closed off in order to inhibit any "short circuiting" between the lumens. However, under certain operating conditions or operating modes, "short circuiting" between the lumens is desired or can be advantageous. Accordingly, in some embodiments of catheter 300, the applied pressure and suction are adjusted for priming or removing the contents of lumens 306 and 352 or for filling lumens 306 and 352 with fluids and/or material prior to use at the tissue site. In such embodiments, one of lumens 306 and 352 is pressurized and/or suction is applied in the other lumen, and the applied pressure and/or suction are adjusted so as to induce "short circuiting" between the lumens and to inhibit the flow of fluid and/or material through macroporous coil 122.

FIG. 8 illustrates exemplary flow paths of fluids and/or materials across macroporous coil 122 and within lumens 306 and 352 in a portion of macroporous section 304 in accordance with a non-limiting exemplary embodiment of catheter 300 wherein lumen 306 is used for aspiration and lumen 352 is used for infusion. It will be apparent to those skilled in the art that the exemplary flow patterns illustrated in FIG. 8 are representative of the flow pattern along the entire effective length 130 of macroporous section 304. Of course, the flow patterns will be affected to a certain extent by any clogging or obstruction at any one or more points or locations anywhere along effective length 130 of macroporous section 304. As shown, during the infusion mode of operation, fluid and/or material introduced under pressure into lumen 352 through the corresponding fitting in connector 320 flows along flow paths 354 to distal region 350 of tube 344, through openings 346, through the porous wall of macroporous coil 122, and into the area (not shown) surrounding macroporous section 304 of catheter 300. And, during the aspiration mode of operation, fluid and/or material in the area (not shown) surrounding macroporous section 304 of catheter 300 flows along flow paths 346, through the porous wall of macroporous coil 122, into lumen 306, and out through the corresponding fitting in connector 320. Although not shown, and as previously stated, the functionalities of lumens 306 and 352 are reversible in some non-limiting exemplary embodiments of catheter 300.

While FIGS. 6-9 illustrate an embodiment of catheter 300 wherein macroporous section 304 does include an internal or external support structure or tube such as that described in the foregoing with reference to the non-limiting exemplary embodiments of catheters 100 and 200, this does not always have to be the case. As such, alternate embodiments of the invention include catheter 300 wherein an internal support tube is longitudinally circumscribed by macroporous coil 122, or an external support structure longitudinally circumscribes macroporous coil 122, or any combination thereof. Further embodiments of the invention include catheter 300 wherein, either one or both internal and external support structures are either radially spaced apart or are not radially spaced apart from macroporous coil 122. Of course, the walls of all such internal or external support structures are configured for facilitating the flow of fluids and/or materials thereacross and, as such, will include one or more of a porous structure or one or more openings. All alternative and/or additional configurations that may become apparent to those skilled in the art are considered as falling within the metes and bounds of the instant invention.

Figure 10:
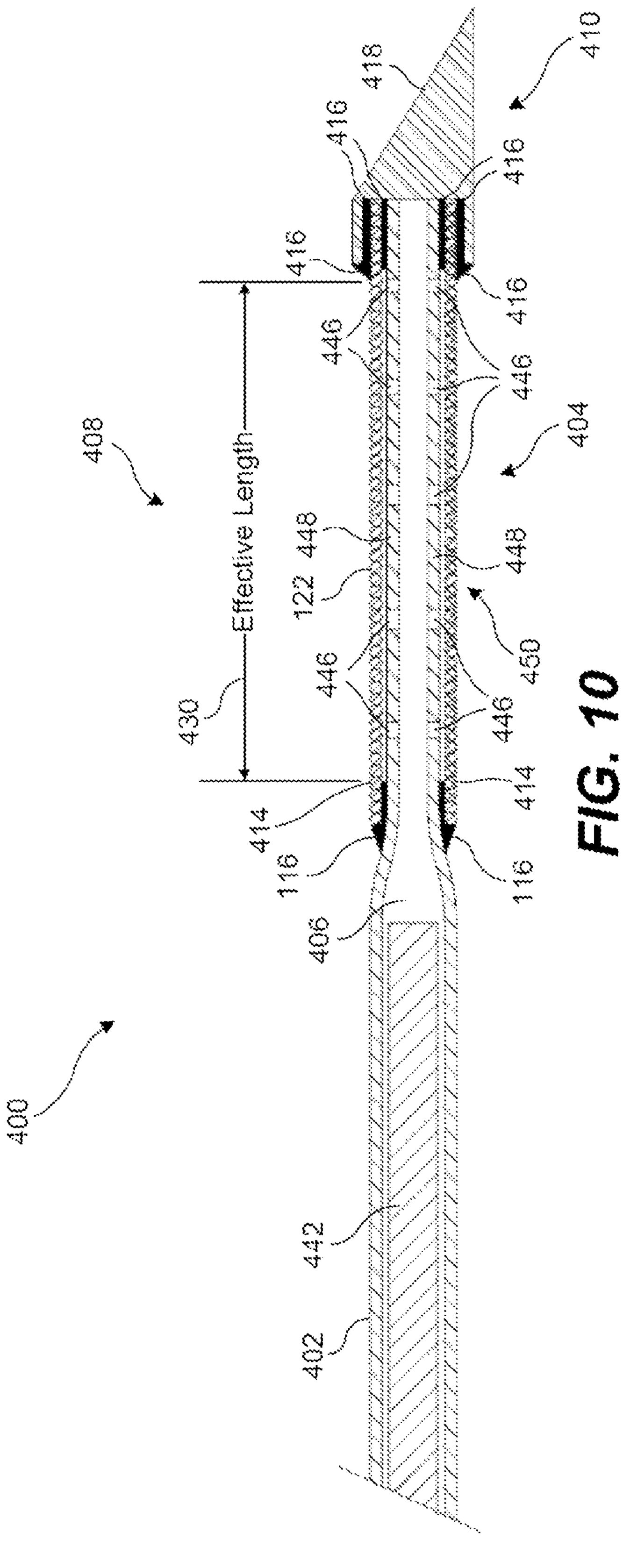
FIG. 10 is a longitudinal cross-sectional view of a distal region of an embodiment of a self-introducing catheter.

FIG. 10 is a longitudinal cross-sectional view of a distal region of an embodiment of self-introducing catheter 400. As will be apparent to one skilled in the art, a self-introducing catheter such as catheter 400 can provide one or more of several benefits including, and not limited to, faster delivery of macroporous section 404 to the tissue site of interest because it does not necessitate the use of an introducer, a relatively smaller profile or "footprint" in contrast to catheters that require an introducer, and in turn, is relatively less invasive than other types of catheters, and a tighter tissue fit with macroporous section 404 without use of an introducer for improved fluid flow between the tissue and the catheter.

Self-introducing catheter 400 is defined, at least in part, by catheter body 402, macroporous coil 122, longitudinally extending lumen 406, and end piece 418 at distal end 410 of catheter 400. As illustrated, distal region 408 of catheter 400 includes macroporous section 404 having an effective length 430 along which fluid and/or material is aspired or infused at a tissue site. Macroporous section 404 is defined, at least in part, by distal region 450 of catheter body 402 longitudinally circumscribed by macroporous coil 122. Distal region 450 of catheter body 402 includes a plurality of openings 446 such as slots or perforations through wall 448 of catheter body 402. As such, during the infusion mode of operation, fluid and/or material introduced under pressure into lumen 406 at a proximal end of catheter 400 will flow to distal region 450 of catheter body 402, through openings 446, through the porous wall of macroporous coil 122, and into the area (not shown) surrounding macroporous section 404 of catheter 400. And, during the aspiration mode of operation, fluid and/or material in the area (not shown) surrounding macroporous section 404 of catheter 400 flows through the porous wall of macroporous coil 122, through openings 446 into lumen 406, and suctioned out through the proximal end of catheter 400.

End piece 418, in an embodiment of self-introducing catheter 400 is a sharp needle tip for ease of penetrating the tissue. As shown, end piece 418 is securely attached to the distal ends of catheter body 402 and macroporous coil 122 using a suitable medical grade adhesive as will become apparent to those skilled in the art, including an epoxy or urethane, or using a weld, braze or solder joint when metallic material are used.

Catheter 400 includes stylet 442 extending longitudinally within lumen 406. In general, stylet 442 is configured for imparting rigidity for easing the introduction of end piece 418 through or into the tissue. In some embodiments, stylet 442 is used for introducing catheter 400 and then removed after macroporous section 404 is positioned at the tissue site. In other embodiments, stylet 442 is not removed or only partially extracted after macroporous section 404 is positioned at the tissue site. In yet other embodiments, stylet 442 is the same as or substantially the same as the various embodiments of core wire 142 as previously described. Accordingly, stylet 442, in some embodiments, is a hollow tube defining a lumen therewithin.

While FIG. 10 illustrates a distal end of stylet 442 terminating proximally of proximal end 414 of macroporous section 404, this does not always have to be the case. In some embodiments of the invention, the distal end of stylet 442 extends longitudinally to proximate end piece 418 at distal end 410 of catheter 400. Regardless of its longitudinal extent, stylet 442, as with core wire 142, is of sufficient rigidity to facilitate the introduction or penetration of catheter 400, aided by end piece 418, into the tissue. In some embodiments, the distal end of stylet 442 is attached or secured to end piece 418 and, as such, facilitates both the insertion and removal of catheter 400. In other embodiments, the distal end of stylet 442 is not secured or attached to end piece 418 and is therefore extractable or removable from catheter 400 after macroporous section 404 has been positioned at the target tissue as desired. In certain embodiments of the invention, stylet 442 is a hollow tube defining a lumen extending longitudinally therewithin, wherein a distal region of stylet 442 may or may not include openings such as openings 346, 446 through a wall of the tube.

In view of the foregoing, it can be seen that several alternative configurations are contemplated as being within the spirit, scope and intent of the disclosed invention. Furthermore, additional configurations may become apparent to those skilled in the art. Accordingly, all variations and/or additional configurations are considered as falling within the metes and bounds of the instant invention.

What is claimed is:

1. A catheter for use in delivering and/or recovering materials to and/or from a tissue site in a body, the catheter comprising:

a macroporous region formed of a helical hollow strand having a proximal end and a distal end and providing a lumen, the macroporous region being coupled to a catheter body at or near its proximal end; and a tube extending within the lumen of the helical hollow strand from the proximal end to the distal end of the helical hollow strand, the tube comprising a wall having a plurality of openings through the wall of the tube.

2. A catheter according to claim 1, wherein the macroporous region comprises a helical hollow wire strand.

3. A catheter according to claim 2, wherein the plurality of openings through the wall of the tube are distributed along a longitudinal extent of the tube and wherein the macroporous region and the tube are adapted to permit the even flow of material through the helical hollow wire strand.

4. A catheter according to claim 3 wherein the catheter further comprises a sharp end piece securely attached to a distal end of the catheter and adapted for penetrating the tissue.

5. A catheter according to claim 4 wherein the tube comprises a support tube having sufficient rigidity to facilitate the penetration of the catheter into the tissue site.

6. A catheter according to claim 5 wherein the end piece is adapted to be sufficiently sharp and wherein the inner tube is adapted to be sufficiently rigid for the catheter to be a self-introducing catheter which may penetrate and be inserted into the tissue without the use of an introducer.

7. A catheter according to claim 1, wherein the catheter comprises at least one macroporous region that is substantially non-inflatable.

8. A catheter according to claim 1 wherein the tube comprises a rigid support tube.

9. A catheter for use in delivering materials to a tissue site in a body, the catheter comprising:

a macroporous region formed of a helical hollow wire strand having a proximal end and a distal end and providing a lumen, the macroporous region being coupled to a catheter body at or near its proximal end, and a tube extending within the lumen of the helical hollow wire strand from the proximal end to the distal end of the helical hollow strand, the tube comprising a wall having a plurality of openings through the wall, the openings distributed along a longitudinal extent of the tube to permit the even flow of material through the helical hollow wire strand to the tissue site.

10. A catheter according to claim 9, wherein the tube comprises a support tube having sufficient rigidity to facilitate the penetration of the catheter into the tissue site.

11. A catheter according to claim 10 further comprising a sharp end piece securely attached to a distal end of the catheter adapted for penetrating the tissue.

12. A catheter according to claim 11 wherein the end piece is adapted to be sufficiently sharp and wherein the inner tube is adapted to be sufficiently rigid for the catheter to be a self-introducing catheter which may penetrate and be inserted into the tissue without the use of an introducer.

13. A method of preparing a catheter according to claim 3 to deliver a medicament to the tissue site, the method comprising the steps of:

providing a medicament in fluid communication with the catheter;

inserting the catheter into the tissue; and infusing the medicament through the tube and then evenly out through the macroporous region into the tissue site.

14. A method of using a catheter according to claim 6, comprising the steps of:

penetrating the body using the distal tip;

inserting the catheter directly into the tissue without the use of an introducer; and positioning the macroporous region at the tissue site.

15. A method of preparing a catheter according to claim 9 to deliver a medicament to the tissue site, the method comprising the steps of:

providing a medicament in fluid communication with the catheter;

inserting the catheter into the tissue; and infusing the medicament through the tube and then evenly out through the macroporous region into the tissue site.

16. A method of using a catheter according to claim 12, comprising the steps of:

penetrating the body using the distal tip;

inserting the catheter directly into the tissue without the use of an introducer; and positioning the macroporous region at the tissue site.

* * * * *